United States Patent [19]

Bruzzese et al.

[11] Patent Number: 5,496,945
[45] Date of Patent: Mar. 5, 1996

[54] PROCESS FOR THE SYNTHESIS OF 9-(2-HYDROXYETHOXY METHYL) GUANINE

[75] Inventors: Tiberio Bruzzese; Giuseppe Guazzi, both of Milan; Marco Rognoni, Lodivecchio; Giuliano Marcon, Erba, all of Italy

[73] Assignee: Solar Chemical S.A., Luxembourg, Luxembourg

[21] Appl. No.: 261,053

[22] Filed: Jun. 13, 1994

[30] Foreign Application Priority Data

Jun. 14, 1993 [IT] Italy .................................. MI93A1264

[51] Int. Cl.$^6$ .................................................. C07D 473/18
[52] U.S. Cl. .................................................. 544/276
[58] Field of Search ............................................. 544/276

[56] References Cited

U.S. PATENT DOCUMENTS 5,223,619  6/1993  Alhede et al. ........................... 544/276
5,336,770  8/1994  Shiragami .............................. 544/276

OTHER PUBLICATIONS

Hakimelahi, Helv. Chim. Acta 72, 1495 (1989).

*Primary Examiner*—Mark L. Berch
*Attorney, Agent, or Firm*—Griffin, Butler Whisenhunt & Kurtossy

[57] ABSTRACT

A process for the synthesis of 9-(2-hydroxyethoxy methyl) guanine in which guanine, or its salts, is reacted with 2–4 moles of hexamethyldisilazane, in the presence of an aprotic solvent and of ammonium sulfate. Thereafter, the trimethylsilyl derivative, without being isolated, is reacted with a stoichiometric quantity of an acyloxyethoxy methyl halide and hydrolyzed with aqueous sodium acetate or sodium hydroxyde to give 9-(2-hydroxyethyoxy methyl) guanine.

10 Claims, No Drawings

PROCESS FOR THE SYNTHESIS OF 9-(2-HYDROXYETHOXY METHYL) GUANINE

Subject of the present invention is a new process for the synthesis of 9-(2-hydroxyethoxy methyl) guanine (acyclovir) a purine derivative having the following structure (I)

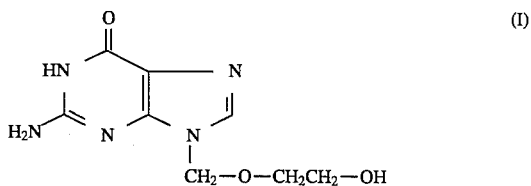

BACKGROUND OF THE INVENTION

Of the purine and pyrimidine derivatives having an open oxygenated chain at the nitrogen atom, which can be considered nucleoside analogues with open sugar substituent, 9-(2-hydroxyethoxy methyl) guanine was found particularly effective in the treatment of diseases due to viral agents such as herpes simplex virus, herpes zoster virus and Epstein-Barr virus. More recently its usefulness was ascertained, in combination with other drugs, for the management of pathologies originated by retrovirus.

9-(2-hydroxyethoxy methyl) guanine was disclaimed by the British Patent no. 1523865 in 1974. Its preparation, described in Example no. 6 of the foregoing patent, is carried out by refluxing overnight guanine with a very large excess of hexamethyldisilazane (HMDS) (59 moles of HMDS per 1 mole of guanine), to obtain a 2,6,9-trimethylsilyl guanine derivative. The reaction is favoured by the presence of ammonium sulphate in a more than catalytic quantity (0.86 moles).

The HMDS excess is rendered indispensable by the nearly total guanine insolubility, only slowly and gradually dissolving as it reacts with HMDS. The excess of HMDS must then be eliminated by vacuum distillation, leading to extensive degradation, such as to hinder its recovery.

The raw silyl derivative is dissolved in benzene; elimination of ammonium sulphate is then carried out by filtration; triethylamine in benzene and 1 mole of 2-benzoyloxyethoxymethyl chloride are then added (II)

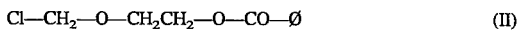

and the mixture is allowed to reflux overnight. Following evaporation of the solvent 2,6-bis (trimethylsilyl)-9-benzoyloxyethoxymethyl-guanine is obtained and the silylated protection groups are therefrom eliminated by brief reflux in ethanol. 9-benzoyloxyethoxymethyl guanine (III), obtained by evaporation of the ethanol, must be thoroughly washed with water, dried and twice crystallized, first from methanol and then from water.

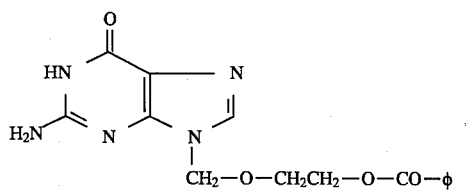

The resulting derivative is finally treated in a pressure reactor with methanolic ammonia at 80° C., so 9-(2-hydroxyethoxymethyl) guanine (I) is obtained, to be recrystallized from methanol.

All in all the process is very long and time consuming. Its complicated method entails the use of several reactors, even under pressure, and of various solvents, wasting of a costly reagent (HMDS), the necessity to crystallize the intermediate (III) twice, from methanol and from water, and the final product (V) from methanol, specially because of the formation of an isomer in which the oxygenated chain is bound to nitrogen in the position 7.

Moreover, the yields are definitely unsatisfactory: the yield of the intermediate (III) is 14% of the theoretical and the yield of the final product (I) is 75% with a total yield of 10.33% even though, according to a variance given in the same example no. 6, the use of an excess (1.6 moles) of the intermediate (II) increases the yield of (III) to 32% and the overall yield to 24.9%.

At any rate the yield remains absolutely insufficient and considered impossible to improve, so much so that the assignees of that patent attempted to realize an alternative syntheses. In fact, a later U.S. Pat. No. 4146715, discloses a new and more satisfactory process for the synthesis of 9-(2-hydroxyethoxy methyl) guanine (I) based on the treatment of $N_2$, 9-diacylated guanine derivatives with reagents able to introduce the 2-acyloxyethoxymethyl chain in position 9. An additional process of hydrolysis leads to the final derivative (I), with industrially acceptable yields (56% and 75% respectively in the two specific preparation examples quoted), starting from the above mentioned $N_2$, 9-diacylated guanine derivatives, which, at any rate, are to be laboriously prepared apart.

Spanish Patent no. 528049 reports more or less the same procedure of the previous British Patent no. 1523865 since, for instance, silylation of guanine is carried out with large quantities of pure HMDS, followed by alkylation under uncontrolled conditions, reflux in ethanol for deprotection from silyl radicals and final aminolysis in alcohol, all the procedure being reported with uncertain yields and no improvement over the prior art.

SUMMARY OF THE INVENTION

In reviewing the preparation of 9-(2-hydroxyethoxy methyl) guanine it was surprisingly noticed that the reaction between guanine and HMDS occurs without the need of using large excesses of the costly silylated reagent, if the operation is conducted in the presence of an aprotic solvent, such as, e.g., xylene ( or a mixture of the 3 isomers ), or other substituted benzenes (chlorobenzene, dichlorobenzene). At most advantageous terms, a guanine mole (151 g) is refluxed with only 2.8–3.0 moles of HMDS ( corresponding to 452–484 g, e.g., 590–630 ml) (instead of 9.52 kg, e.g., 12.44 litres as foreseen according to British Patent no. 1523865) , in an equal volume of xylene. In this case too the presence of ammonium sulphate is useful, but in truly catalytic quantities (0.076 moles). After a few reflux hours the starting suspension turns to a silyl derivative solution.

It was also surprisingly found that the use of particular guanine salts, such as the sulphate can definitely accelerate the speed and completion of the silylation reaction. In this case, therefore, the addition of ammonium sulphate may become unnecessary, moreover, the silylation reaction would take only a few hours (e.g., 1–3 hours) instead of 12–24 hours or more.

The use of guanine salts (hydrochloride or better still sulphate) is even more important and advantageous since they are usually obtained as the intermediate phase in the hydrolysis process of guanosine to guanine through hydrochloric or sulphuric acid: in other words, guanine sulphate, for instance, is a more economic intermediate for the production of guanine base starting from guanosine.

Furthermore, it was also surprisingly found that the subsequent reaction of the silyl derivative of guanine with an acyloxyethoxy methyl halide, such as acetoxyethoxy methyl chloride or preferably bromide (IV)

$$Br-CH_2-O-CH_2CH_2-OCOCH_3 \quad (IV)$$

for a brief period of time (e.g., 0.5 to 5 hours ), at a moderate temperature (e.g., 50° to 100 ° C.), followed by a hydrolytic treatment in situ (one step, one pot) with sodium acetate or sodium hydroxide water solution to remove the silylated radicals, leads directly and without further manipulation, to 9-(2-acetoxyethoxy methyl) guanine (V)

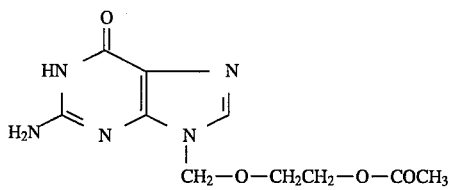

DESCRIPTION OF PREFERRED EMBODIMENTS

That the reaction between silylated guanine and reagent (IV) is a process substantially differing from the reaction with reagent (II) described in British Patent no. 1.523.865 is proved not only by the fact that the use of a practically stoichiometric quantity of (IV) (1.04 moles) leads to a highly satisfactory yield (70–76%) of (V), but also by the fact that the use of a quantity of (IV) in excess of the theoretical, lowers the yield and gives a less pure product, in divergence with the contents of the British Patent.

The conditions described for the condensation reaction between tris (trimethylsilyl) guanine and acyloxyethoxy halide (temperature, reaction mean HMDS+ xylene, etc), allow a high N9 'regiospecificity' (substitution ratio N9/N7= 99:1), while, on the other hand, the conditions described in literature lead to mixtures of the two isomers N9/N7 in the ratio 90/10 or lower and, at any rate, with rather low yields.

Under the foregoing conditions, derivative (V) is obtained in such a pure state that it can be transformed to the final 9-(2-hydroxyethoxy methyl) guanine with an extremely simple and economic procedure.

1) According to the invention, intermediate (V) undergoes separation through filtration and subjected to hydrolysis with aqueous NaOH, with no purification treatment, at room—or a little higher—temperature ( 20°–50 ° C.) . The yield of intermediate (V) is 73%, that of the hydrolysis step is 100%, therefore the overall yield is 73%.

2) In alternative, after that water and aqueous NaOH have been added to the reaction mixture containing the intermediate (V), up to alkalinity, the aqueous phase containing the intermediate is separated and kept at room temperature (or slightly higher ) for 0.5–4 hours, up to total hydrolysis to 9-(2-hydroxyethoxy methyl) guanine.

3) According to another variation of the process, the alkaline water solution of intermediate (V) is adsorbed on anionic resins, then eluted with aqueous NaOH to obtain the final hydrolyzed product.

It is to be stressed that, according to procedures 2) and 3), the entire process of synthesis of 9-(2-hydroxyethoxy methyl) guanine is carried out in one step only and in one reactor only, with obvious economic and technologic advantages, obtaining in each case a product meeting the purity requirements of the major pharmacopoeias. Interestingly enough is the fact that the resulting product contains only traces, if at all present, of the isomer having the side-chain bound in position 7, the O-acetylated precursor of which also forms just after the addition of reagent (IV) to the reaction mixture, but during the process it transposes to the derivative substituted at position 9.

If so desired, further improvement of the already high purity of the final product (I) can be obtained by simple crystallization from water.

In addition to the novelty elements as compared to British Patent no. 1.523.865, the process that is the subject of the present invention offers a series of practical and economic advantages, such as use of very small quantities of HMDS, therefore with much lower costs as well as less technical and economical difficulty in disposing of large quantities of the reagent; use of organic solvents easily and economically recovered; avoidance of ammonium sulphate filtration (the catalytic quantity used in the present process dissolves in the sodium acetate solution used for hydrolysis to (V), and is eliminated with the mother waters); triethylamine elimination in the alkylation reaction yielding intermediate (V); obtainment of very pure (V), almost free from isomers and not requiring purification; simple (V) hydrolysis in aqueous sodium hydroxide instead of aminolysis under pressure of (III); the possibility of performing the entire process in one stage and in one reactor only; elimination of methanol as crystallization solvent.

The possibility of using, in the invention process, some guanine salts (preferably sulphate) instead of guanine base, affords further unexpected advantages in terms of lower reagent costs (guanine sulphate is the intermediate of the hydrolytic process from guanosine to guanine), and of increased speed of the silylation reaction, while using very low quantities of HMDS and not damaging the stereoselectivity of the reaction (absence of reaction in position 7).

The following examples will illustrate the invention without however limiting it in any way.

EXAMPLE 1

20 kg of guanine, 61.6 kg of hexamethyldisilazane, 80 litres of xylene and 1.33 kg of ammonium sulphate are refluxed overnight. The resulting clear solution is cooled to room temperature, added with 27 kg of acetoxyethoxymethyl bromide and maintained at 90° C. for 45 minutes, then cooled to room temperature and added with 1500 litres of a 20% sodium acetate water solution.

Allow to stir for a short time to obtain a 9-(2-acetoxyethoxy methyl) guanine precipitate, which is filtered from the two immiscible liquid phases. The yield in anhydrous dried product is 25.9 kg (73% of the theoretical). However, without the need for drying, the still moist product is added to a mixture made up of 400 litres of water and 25 litres of 30% sodium hydroxyde then allowed to stand for 2 hours at room temperature up to total hydrolysis. Finally, the addition of 10 litres of 36% hydrochloric acid leads to the formation of a 9-(2-hydroxyethoxy methyl) guanine precipitate, which is filtered and, still moist, crystallized from 400 litres of water. After drying 22.9 kg of product having 5% moisture are obtained, corresponding to 21.8 kg anhydrous.

M.p.=255°–7° C. the other characteristics comply with a reference standard sample.

The yield of 9 -(2-hydroxyethoxy methyl) guanine hydrolysis is 100%, the process overall yield is 73%.

EXAMPLE 2

20 kg of guanine, 61.6 kg of hexamethyldisilazane, 80 litres of xylene and 1.33 kg of ammonium sulphate are allowed to reflux overnight. The resulting clear solution is cooled to room temperature, dropwise added with 27 kg of acetoxyethoxy methyl bromide and maintained at 60° C. for 3 hours, then cooled to room temperature, added with 1500 litres of water and treated with conc. NaOH up to pH 12.5. The mixture, made up of 2 phases ( one organic and one aqueous, containing 9-(2-acetoxyethoxy methyl) guanine) is maintained at room temperature for 2 hours up to hydrolysis of the acetoxy derivative. The organic layer is eliminated through suction and 35% hydrochloric acid is added up to precipitation of 9-(2-hydroxyethoxy methyl) guanine which is filtered and, still moist, crystallized from 400 litres of water.

23.8 kg of product having 5% moisture (after drying) are obtained, corresponding to 22.6 kg anhydrous.

M.p.=255°–7° C.

The process overall yield is 76%.

EXAMPLE 3

50 kg of guanine, 150 kg of hexamethyldisilazane, 200 litres of xylene and 3.5 kg of ammonium sulphate are allowed to reflux till complete solution is attained. Cool the solution to room temperature and add 70 kg of acetoxyethoxy methyl chloride. The mixture is reacted at 60° C. for 2 hours then added to 5000 litres of hot water.

The organic phase is separated, the aqueous phase is adsorbed on anionic resin, then eluted with sodium hydroxide and the fractions collected as 9-(2hydroxyethoxy methyl) guanine. The combined aqueous fractions are concentrated through nanofiltration membranes.

The concentrate is neutralized with hydrochloric acid and precipitation of the final product is thus obtained.

M.p.=256° C.

The yield is 52.2 kg, equivalent to 70% of the theoretical.

EXAMPLE 4

Guanine sulphate (30 kg) is suspended in 110 litres of xylene and 85.8 kg of hexamethyldisilazane is added at one time. The reaction mixture is heated to reflux (int. T=132°–134° C.) for 2 hours obtaining a clear yellowish solution.

It is cooled to 26°–28° C. and, within about 20 minutes, acetoxyethoxy methyl bromide (25 kg) is added, maintaining the temperature at 29°–30° C. with external cooling.

After having added acetoxyethoxy methyl bromide the reaction mixture is heated to an internal temperature of 68°–72° C. for 1 h and 30'. Again cooled to 28°–30° C. and poured into a solution of 30% NaOH (50 litres) in $H_2O$ (700 liters) with brisk stirring. The resulting pH is 10.8 and is adjusted to 12.5 by the addition of 30% NaOH over a period of 60 minutes.

After 1 more hour under agitation at 25° C. the phases are separated. The aqueous phase is neutralized to pH 7 with conc. HCl. The white, dense precipitate is heated to reflux and maintained under agitation at that temperature for 20 minutes. The mixture is filtered while boiling and the filtrate is allowed to crystallize slowly to an internal temperature of 0°. Filter and thoroughly wash with cold water.

Vacuum drying at 60° C. overnight yields 17.7 kg of white crystalline product that is 9-(2-hydroxyethoxy methyl) guanine.

EXAMPLE 5

A mixture of guanine (15.1 kg), ammonium sulphate (800 g), hexamethyldisilazane (46.5 kg) in 68 liters of xylene is heated to reflux (136°–138° C.) to obtain a clear solution. Cool to room temperature.

An acetyl bromide (13 kg) and 1.3-dioxolane (7.5 kg) mixture is prepared apart, and maintained in reaction at 15°–20° C. for a few hours, thus obtaining acetoxyethoxy methyl bromide.

The silylated guanine solution is added with the acetoxyethoxymethyl bromide derivative previously prepared and the reaction mixture is heated to 70° C. for 2 hours.

Once the condensation reaction has ended the temperature is allowed to cool.

The reaction mixture is poured into 60 liters of water then added with sodium hydroxide to a pH of 11.5–12. The organic phase is separated.

The aqueous phase is loaded into an anion resin column (600 liters). Elution is carried out with dilute sodium hydroxide: the fraction containing 9-(2-hydroxyethoxy methyl guanine is collected.

The aqueous fraction containing the product in the form of sodium salt, highly pure and practically free from isomers, is concentrated by reverse osmosis through nanofiltration membranes.

The concentrated solution is precipitated to pH 7 with hydrochloric acid, thus precipitation of the final product occurs. The product is collected by filtration, washed with water and dried.

Yield=15.2 kg M.p.=256° HPLC assay value=99%

We claim:

1. A process for the synthesis of 9-(2-hydroxyethoxy methyl) guanine, comprising reacting guanine, or a salt thereof with between 2 and 4 moles of hexamethyldisilazane, in the presence of an aprotic solvent and of a catalytic amount of ammonium sulphate; reacting the resulting guanine trimethylsilyl derivative, without being isolated, with a stoichiometric quantity of acyloxyethoxy methyl halide at a temperature of 50° to 100° C.; and hydrolyzing with a sodium acetate or sodium hydroxyde water solution the resulting 9-(2-acetoxyethoxy methyl) guanine, to provide 9-(2-hydroxyethoxy methyl) guanine.

2. A process, according to claim 1, wherein the entire process is conducted, without isolation of any intermediate.

3. A process, according to claim 1, wherein the ratio of hexamethyldisilazane to guanine is about 2.8–3 moles per mole.

4. A process, according to claim 1, wherein the solvent used in the reaction between guanine and hexamethyldisilazane is xylene.

5. A process, according to claim 4, wherein that the reaction between guanine and hexamethyldisilazane occurs at the xylene boiling temperature.

6. A process, according to claim 1, wherein acyloxyethoxy methyl halide is acetoxyethoxy methyl bromide.

7. A process, according to claims 1, wherein the molecular ratio between the guanine trimethylsilyl derivative and acetoxyethoxy methyl bromide is 1:1.1.

8. A process according to claim 1, wherein hydrolysis of 9-(2-acetoxyethoxy methyl) guanine intermediate with NaOH is conducted at room temperature.

9. A process, according to claim 1, wherein the guanine salt is guanine sulphate.

10. A process, according to claim 1, wherein 9-(2-acetoxyethoxy methyl) guanine is hydrolyzed and adsorbed on anionic resin then 9-(2-hydroxyethoxy methyl) guanine is eluted with NaOH and recovered through concentration and neutralization.

* * * * *